US009686981B2

(12) United States Patent
Kiesel et al.

(10) Patent No.: US 9,686,981 B2
(45) Date of Patent: *Jun. 27, 2017

(54) COUPLERS FOR MEDIUM-CHAIN FATTY ACIDS AND DISINFECTING COMPOSITIONS

(71) Applicant: Ecolab USA Inc., St. Paul, MN (US)

(72) Inventors: Elizabeth Kiesel, St. Paul, MN (US); Michael E. Besse, Golden Valley, MN (US); Lisa A. Hellickson, Rosemount, MN (US); Mark Levitt, Lake Elmo, MN (US); Daniel E. Pedersen, Cottage Grove, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,914

(22) Filed: Mar. 9, 2015

(65) Prior Publication Data

US 2015/0173352 A1 Jun. 25, 2015

Related U.S. Application Data

(63) Continuation of application No. 13/104,549, filed on May 10, 2011, now Pat. No. 9,006,286.

(51) Int. Cl.
| | | |
|---|---|---|
| *A01N 37/00* | (2006.01) | |
| *A61K 31/201* | (2006.01) | |
| *A01N 25/30* | (2006.01) | |
| *C11D 1/44* | (2006.01) | |
| *C11D 3/20* | (2006.01) | |
| *C11D 3/48* | (2006.01) | |
| *C11D 10/04* | (2006.01) | |
| *A01N 37/02* | (2006.01) | |
| *C11D 1/66* | (2006.01) | |
| *C11D 1/72* | (2006.01) | |

(52) U.S. Cl.
CPC ............. *A01N 25/30* (2013.01); *A01N 37/02* (2013.01); *C11D 1/44* (2013.01); *C11D 1/66* (2013.01); *C11D 1/72* (2013.01); *C11D 3/2079* (2013.01); *C11D 3/48* (2013.01); *C11D 10/045* (2013.01)

(58) Field of Classification Search
CPC ........ A01N 25/30; A01N 37/02; A01N 37/06; A01N 37/44; C11D 10/045; C11D 1/44; C11D 1/66; C11D 1/72; C11D 3/2079; C11D 3/48
See application file for complete search history.

(56) References Cited

U.S. PATENT DOCUMENTS

| | | | |
|---|---|---|---|
| 4,895,667 A | 1/1990 | Fox et al. | |
| 5,208,257 A | 5/1993 | Kabara | |
| 5,234,719 A | 8/1993 | Richter et al. | |
| 5,436,008 A | 7/1995 | Richter et al. | |
| 5,490,992 A | 2/1996 | Andrews et al. | |
| 5,994,280 A | 11/1999 | Giret et al. | |
| 6,060,625 A | 5/2000 | Su et al. | |
| 6,063,145 A | 5/2000 | Larkin et al. | |
| 6,077,816 A | 6/2000 | Puvvada et al. | |
| 6,350,725 B1 | 2/2002 | Levitt et al. | |
| RE37,866 E | 10/2002 | Wright et al. | |
| 7,341,983 B2 | 3/2008 | Pedersen et al. | |
| 2003/0096726 A1 | 5/2003 | Smith et al. | |
| 2005/0032668 A1* | 2/2005 | Pedersen ................ | A01N 37/02 510/499 |
| 2007/0119529 A1 | 5/2007 | Hobson et al. | |
| 2007/0219099 A1 | 9/2007 | Morales Arriaga | |

FOREIGN PATENT DOCUMENTS

| | | |
|---|---|---|
| EP | 0662783 A | 7/1995 |
| EP | 0662783 | 7/1997 |
| EP | 0887401 | 12/1998 |
| EP | 1023423 | 2/2004 |
| GB | 2391810 | 2/2004 |
| JP | 0135898 A2 | 4/1985 |
| JP | 0135898 A3 | 4/1985 |
| JP | 1992013799 | 1/1992 |
| JP | 1996503209 | 4/1996 |
| JP | 1997501427 | 2/1997 |
| JP | 199236588 | 8/1999 |
| JP | 2003505446 | 2/2003 |
| JP | 2007501228 | 1/2007 |
| JP | 2007161776 | 6/2007 |
| JP | 2008081428 | 4/2008 |
| WO | 9504459 | 2/1995 |
| WO | 9531100 | 11/1995 |
| WO | 0041567 | 7/2000 |
| WO | 2005015996 A1 | 2/2005 |

OTHER PUBLICATIONS

Friedli, Detergency of Spcialty Surfactants, vol. 98, 2001.*

(Continued)

*Primary Examiner* — Jean Cornet
(74) *Attorney, Agent, or Firm* — McKee, Voorhees & Sease, PLC

(57) ABSTRACT

A disinfecting shower cleaner composition including a medium-chain fatty acid coupled with a nonionic surfactant providing temperature stable antimicrobial compositions. The invention specifically relates to antimicrobial compositions including fatty acid antimicrobial agents coupled with an ethoxylated amine and methods of using the antimicrobial compositions.

13 Claims, No Drawings

(56) References Cited

OTHER PUBLICATIONS

Mirgorodskaya, A.B. et al., "The Solubilization of Fatty Acids in Systems Based on Block Copolymers and Nonionic Surfactants" Physical Chemistry of Solutions, Russian Journal of Physical Chemistry A, 2010, vol. 84, No. 12, pp. 2066-2070.
Ecolab USA Inc. et al., PCT/IB2012/052289, "Notification of Transmittal of International Search Report and the Written Opinion of the International Searching Authority, or the Declaration", mailed Jan. 30, 2013.
AkzoNobel, Surface Chemistry, 2010.
European Patent Office, "European Supplementary Search Report Communication", Issued in connection to International Application No. PCT/IB2012/052289, mailed Jul. 8, 2015, 7 pages.
European Patent Office, "Communication", issued in connection with Application No. 127829257, mailed Jun. 14, 2016, 6 pages.
European Patent Office, "extended European Search Report" issued in connection to International Application No. PCT/IB2012/052289, 7 pages, mailed Jul. 8, 2015.

\* cited by examiner

COUPLERS FOR MEDIUM-CHAIN FATTY ACIDS AND DISINFECTING COMPOSITIONS

CROSS REFERENCE TO RELATED APPLICATIONS

This is a Continuation application of U.S. Ser. No. 13/104,549 filed May 10, 2011, herein incorporated by reference in its entirety.

FIELD OF THE INVENTION

The invention relates to antimicrobial compositions including carboxylic acids, such as fatty acid antimicrobial agents, and a non-ionic surfactant, such as an ethoxylated amine. The compositions can be used to clean surfaces, including for example, a solid shower cleaner and disinfectant composition and methods of use thereof.

BACKGROUND OF THE INVENTION

There is a longstanding need for antimicrobial agents having improved efficacy and non-irritating and non-corrosive characteristics. The specific requirements for such agents vary according to the intended application (e.g., sanitizer, disinfectant, cleaner, sterilant, etc.) and the applicable public health requirements. For example, as set out in Germicidal and Detergent Sanitizing Action of Disinfectants, Official Methods of Analysis of the Association of Official Analytical Chemists, a sanitizer should provide a 99.999% reduction (5-log order reduction) within 30 seconds at room temperature against several test organisms, whereas a disinfectant should kill all vegetative cells including most recognized pathogenic microorganisms.

There is a further need for antimicrobial compositions in which fatty acid antimicrobial agents are effectively coupled with a surfactant agent to ensure there is no esterification of the fatty acid antimicrobial agent. Conventional compositions of fatty acid antimicrobial agents that are coupled with amines often result in complexing, decreasing the stability of the composition. Often a cloudy composition results indicative of the esterification and loss of antimicrobial activity. Therefore, additional coupling compositions are necessary for fatty acid antimicrobial compositions.

BRIEF SUMMARY OF THE INVENTION

The present invention relates to antimicrobial compositions comprising, consisting of and/or consisting essentially of a fatty acid antimicrobial agent and an ethoxylated amine surfactant or coupling agent, and to methods of using such antimicrobial compositions. An advantage of the invention provides a compatible coupler for saturated fatty acids, such as decanoic acid, in an aqueous solvent. Compositions according to the invention provide a solid, high bio-based, cost-effective, non-irritating and non-corrosive antimicrobial cleaner, which may be used to provide a stable aqueous use solution.

In an embodiment, the invention comprises a composition having from about 0.05 wt-% to about 20 wt-% carboxylic acid antimicrobial agent and from about 0.1 wt-% to about 30 wt-% nonionic surfactant, wherein the nonionic surfactant and carboxylic acid antimicrobial agent have a weight ratio of about 5.5:1 to about 3:1 and the composition is clear and has effective antimicrobial activity.

In a further embodiment, the invention comprises a composition having from about 0.05 wt-% to about 10 wt-% fatty acid antimicrobial agent and from about 0.15 wt-% to about 55 wt-% ethoxylated amine of one of the following formulas:

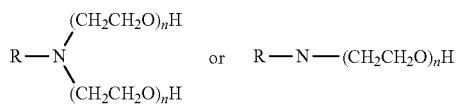

wherein the ethoxylated amine and fatty acid antimicrobial agent being at a weight ratio of about 5.5:1 to about 3:1, and wherein the composition is clear and has effective antimicrobial activity.

In yet a further embodiment of the invention, a method of reducing a microbial population on an object comprises contacting the object with a composition comprising: from about 0.05 wt-% to about 10 wt-% fatty acid antimicrobial agent and from about 0.15 wt-% to about 55 wt-% ethoxylated amine of one of the following formulas:

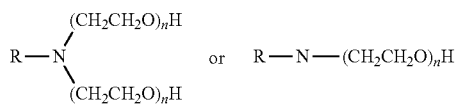

wherein the ethoxylated amine and fatty acid antimicrobial agent being at a weight ratio of about 5.5:1 to about 3:1, and wherein the composition is clear and has effective antimicrobial activity.

In certain embodiments, the compositions can also include additional and optional ingredients, such as a solvent, diluent, sequestrant, acidulant, or other adjuvant such as a stabilizing agent, wetting agent, thickener, foaming agent, pigment and dye, or mixtures thereof.

The compositions and methods of the invention are especially useful as antimicrobial compositions for use as sterilants, sanitizers, disinfectants, soap scum remover, lime remover, delimer, hand wash and sanitizer and other cleaners. The compositions and methods have particular utility as a shower cleaner, disinfectant and sanitizer. The antimicrobial compositions and methods have further utility in a variety of healthcare and food service applications.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENT

The present invention relates to solid shower cleaners and antimicrobial agents, and methods of using the same. The compositions and methods of cleaning therewith provide many advantages over conventional cleaning products. For example, compositions according to the invention provide a solid, highly bio-based, cost-effective, shower cleaner and disinfectant that is both non-irritating and non-corrosive. The present invention provides these numerous advantages along with demonstrating improved efficacy against *Staphy-* lococcus aureus and other bacteria. When applied to microbes (e.g., when applied to a surface containing microbes), the compositions of the invention exhibit antimicrobial action. The mechanism by which such action takes place is not completely understood. However, as shown in the Examples set out below, very rapid and substantially complete antimicrobial action is attained according to the compositions and methods according to the invention.

The embodiments of this invention are not limited to particular compositions and methods of cleaning therewith, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities refers to variation in the numerical quantity that can occur.

Term "antimicrobial composition," as used herein, refers to a composition having the ability to cause greater than a 90% reduction (1-log order reduction) in the population of bacteria or spores. Preferably, the antimicrobial compositions of the invention provide greater than a 99% reduction (2-log order reduction), more preferably greater than a 99.99% reduction (4-log order reduction), and most preferably greater than a 99.999% reduction (5-log order reduction) in such population within 10 minutes at 60° C. Preferably, the antimicrobial compositions of the invention provide greater than a 99% reduction (2-log order reduction), more preferably greater than a 99.99% reduction (4-log order reduction), and most preferably greater than a 99.999% reduction (5-log order reduction) in the population of one or more additional organisms. Because in their broadest sense these definitions for antimicrobial activity are different from some of the current governmental regulations, the use in connection with this invention of the term "antimicrobial" is not intended to indicate compliance with any particular governmental standard for antimicrobial activity.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

As used in this invention, the term "disinfectant" refers to an agent that kills all vegetative cells including most recognized pathogenic microorganisms, using the procedure described in AOAC Use Dilution Methods, Official Methods of Analysis of the Association of Official Analytical Chemists, paragraph 955.14 and applicable sections, 15th Edition, 1990 (EPA Guideline 91-2).

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a high concentration composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used in this invention, the term "microorganisms" refers to any noncellular or unicellular (including colonial) organism. Microorganisms include all prokaryotes. Microorganisms include bacteria (including cyanobacteria and Mycobacteria), lichens, microfungi, protozoa, virinos, viroids, viruses, fungi (e.g., molds and yeast), and some algae. As used herein, the term "microbe" is synonymous with microorganism.

As used herein, the term "object" refers to something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used in this invention, the term "sanitizer" refers to an agent that reduces the number of bacterial contaminants to safe levels as judged by public health requirements. Preferably, sanitizers for use in this invention will provide at least a 99.999% reduction (5-log order reduction) using the Germicidal and Detergent Sanitizing Action of Disinfectants procedure referred to above.

The term "sterilant," as used herein, refers to a physical or chemical agent or process capable of destroying all forms of life (including bacteria, viruses, fungi, and spores) on inanimate surfaces. One procedure is described in AOAC Sporicidal Activity of Disinfectants, Official Methods of Analysis of the Association of Official Analytical Chemists, paragraph 966.04 and applicable sections, 15th Edition, 1990 (EPA Guideline 91-2).

The terms "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The compositions and methods of the present invention may comprise, consist essentially of, or consist of the component and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Compositions Including Medium Chain Fatty Acid Antimicrobial Agents and Suitable Coupling Agents The present invention relates to antimicrobial compositions including antimicrobial agents, namely fatty acids, and a coupling agent, such as an ethoxylated amine. In an embodiment, the combination of the ethoxylated amine and fatty acid antimicrobial agent maintains solubility of the fatty acid within the composition as a result of the solubility profile and HLB of the ethoxylated amine, along with the ratio of the composition components. The fatty acid antimicrobial agent is immediately dispersed and soluble upon dilution with water. In addition, the antimicrobial compositions demonstrate sufficient temperature stability while fully solubilizing the antimicrobial fatty acid. According to an embodiment, the ethoxylated amine coupler for the fatty acid antimicrobial agent is stable at temperatures of at least about 50° F. to 120° F.

According to the invention, a stable and clear composition is formed, retaining the antimicrobial activity of the fatty acid, providing ideal shower and bath disinfectants, detergents and other cleaning compositions. According to an embodiment of the invention, the present composition employs the ethoxylated amine surfactant to effectively couple the fatty acid antimicrobial agent into an aqueous solvent. In an embodiment, the ethoxylated amine is capable of coupling the fatty acid into acidic compositions without complexing or reacting with the fatty acid, forming a clear and stable aqueous use solution that provides effective soil removal.

Antimicrobial Agent

The compositions of the present invention can include an antimicrobial agent such as a lipid, a fatty acid and/or a low HLB antimicrobial agent. Examples of suitable antimicrobial agents include fatty acid or carboxylic acid antimicrobial agents. According to an embodiment of the invention, preferred fatty acid antimicrobial agents include medium chain fatty acids, including $C_6$-$C_{16\ alkyl}$ carboxylic acids, such as hexanoic acid, butyric acid, octanoic acid, heptanoic acid, nonionic acid, and decanoic acid. More preferably, the fatty acid antimicrobial agent an $C_8$-$C_{12}$ alkyl carboxylic acid, still more preferably $C_9$-$C_{10}$ alkyl carboxylic acid, such as decanoic acid (capric acid). It is to be understood that mixtures of antimicrobial agents can be used if desired.

According to additional embodiments of the invention, suitable fatty acid antimicrobial agents include an aliphatic or aromatic fatty acid, either saturated or unsaturated, having from about 6 to about 16 carbon atoms, or mixtures of these fatty acids. In an embodiment, the aliphatic fatty acid is saturated. In an embodiment the fatty acid includes about 8 to about 12 carbon atoms. In an embodiment the fatty acid includes about 9 to about 10 carbon atoms. The fatty acid can be linear, branched or cyclic and can contain substituent atoms such as hydroxyl groups or ether linkages as long as the substituents do not affect antimicrobial activity. Suitable fatty acids include, for example, hexanoic acid, heptanoic acid, octanoic acid, nonanoic acid, decanoic acid, dodecanoic acid, myristic acid, or mixtures thereof. In an embodiment, the fatty acid includes heptanoic acid, octanoic acid, nonanoic acid, decanoic acid, dodecanoic acid, or mixtures thereof. In an embodiment, the fatty acid preferably includes decanoic acid.

The compositions of the invention contain sufficient antimicrobial agent to achieve the desired rate and efficacy for microbial reduction from a solid concentrated composition. The antimicrobial agent can be present in a solid concentrated composition 0.1 to about 35 wt-%, about 0.1 to about 30 wt-%, about 0.1 to about 25 wt-%, about 0.1 to about 20 wt-%, about 0.1 to about 15 wt-%, about 0.1 to about 10 wt-%, about 0.5 to about 10 wt-%, about 0.5 to about 7 wt-%, or about 0.5 to about 5 wt-%. The antimicrobial agent can be present at any of these amounts not as part of a range and/or at any of these amounts not modified by about.

The compositions of the invention may further contain sufficient antimicrobial agent to achieve the desired rate and efficacy for microbial reduction from a use solution composition. The antimicrobial agent can be present in a use composition, such as a use solution at about 0.05 to about 25 wt-%, about 0.07 to about 20 wt-%, about 0.07 to about 5 wt-%, about 0.05 to about 3 wt-%, about 0.07 to about 3 wt-%, about 0.05 to about 15 wt-%, about 0.1 to about 25 wt-%, about 0.1 to about 20 wt-%, about 0.1 to about 10 wt-%, about 0.1 to about 5 wt-%, about 0.1 to about 4 wt-%, about 0.1 to about 3 wt-%, or about 0.1 to about 15 wt-%. The antimicrobial agent can be present at any of these amounts not as part of a range and/or at any of these amounts not modified by about.

The antimicrobial compositions of the invention may optionally be formulated to contain an additional antimicrobial agent. This additional antimicrobial agent can be dissolved or dispersed in the antimicrobially-active solvent or in a diluting solvent. Suitable additional antimicrobial agents include carboxylic acids, diacids, or triacids (e.g., butyric acid, heptanoic acid, octanoic acid, nonanoic acid, decanoic acid, salycic acid, mandelic acid, succinic acid, adipic acid, glutaric acid, EDTA and citric acid or isomers thereof), carboxylic esters (e.g., p-hydroxy alkyl benzoates and alkyl cinnamates), sulfonic acids (e.g., dodecylbenzene sulfonic acid), iodo-compounds or active halogen compounds (e.g., iodine, interhalides, polyhalides, metal hypochlorites, hypochlorous acid, metal hypbromites, hypobromous acid, chloro- and bromo-hydantoins, chlorine dioxide and sodium chlorite), active oxygen compounds including hydrogen peroxide, isolated or equilibrium derived or isolated peracids such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids or diesters (e.g., such as adipic, succinic, glutaric, or malonic acid and mixtures thereof), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and C1-C6 alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

Ethoxylated Amines

A variety of surfactants can be employed for use in the compositions according to the invention to provide a coupler for the fatty acid antimicrobial agent, such as decanoic acid, in an aqueous solvent. In general, the surfactant identity and use level is selected based upon the characteristics of the antimicrobial agent, including the solubility of the fatty acid antimicrobial agent. Preferred compositions according to the invention employ a surfactant with a sufficiently high HLB value to provide adequate solubility, without oversolubilization result in the complexing of the antimicrobial agent (i.e. wherein the antimicrobial agent is within a micelle and unable to provide antimicrobial effects against microbes contacted with the composition). As one skilled in the art appreciates the HLB represents the empirical expression for the hydrophilic and hydrophobic groups of the surfactant, wherein the higher the HLB value the more water-soluble the surfactant.

According to an embodiment the HLB of the surfactant is greater than or equal to about 7 to about 14, preferably from about 7.5 to about 14, more preferably from about 10 to about 14 or from about 11 to about 14, or still further from about 12 to about 14. The surfactant according to the invention does not cause formation of insoluble deposits, and has low odor and low toxicity. Mixtures of surfactants can be used if desired in order to obtain the desired HLB of the one or more surfactants.

In an embodiment, the composition includes a nonionic surfactant, preferably an ethoxylated amine used in combination with the fatty acid antimicrobial. According to the invention, the ratio of the ethoxylated amine to antimicrobial agent is tailored to provide suitable coupling for maintained solubility and antimicrobial activity of the fatty acid component. The ratio of ethoxylated amine to antimicrobial agent ranges from about 9:1 to about 1:1 (ethoxylated amine to fatty acid antimicrobial agent), about 8:1 to about 1:1, about 7:1 to about 2:1, about 6:1 to about 2:1, about 5.5:1 to about 3:1, about 5.5:1 to about 4.5:1, about 4.5:1 to about 3:1, or about 4.5:1. According to a preferred embodiment the ratio of ethoxylated amine to the decanoic acid antimicrobial agent in an aqueous solvent is between about 4.5:1 to about 5.5:1.

The present compositions can include any of a variety of ethoxylated amines. In an embodiment, the ethoxylated amine may be branched or unbranched according to one of the following formulas:

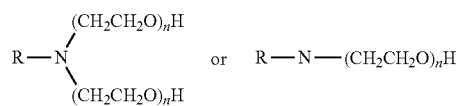

According to the invention R can be a straight or branched alkyl or alkylaryl substituent. R can be a substituent having from 1 to 24 carbon atoms and each n can be from 1 to 20. In an embodiment of the invention, n is from 1 to 16, from 1 to 15, from 1 to 14, from 1 to 13, from 1 to 12, from 1 to 11, from 1 to 10, from 1 to 9, from 1 to 8, from 1 to 6, from 1 to 5, from 1 to 4, or from 1 to 3.

In a further embodiment R is derived from coconut oil and n is between 1 to 14, preferably between 6 to 12 and has an HLB from approximately 10 to 14. In a branched ethoxylated amine according to the invention the total EO groups (n+n) are preferably between 6 to 12 or 6 to 10. In a further embodiment, R can be capped or terminated with ethylene oxide, propylene oxide, or butylene oxide units. A suitable CAS number for an ethoxylated amine according to the invention is 61791-14-8.

According to an embodiment of the invention, the R groups of the ethoxylated amine provide sufficient solubility to stabilize and solubilize the fatty acid antimicrobial agent within an aqueous solution. According to an embodiment of the invention, the surfactant does not include an alcohol and is a medium to short chain carbon group having less than 24 carbon atoms. According to a further embodiment of the invention, the ethoxylated amine is a cocoamine. Ethoxylated cocoamines are commercially available, for example, under tradenames such as Varonic (Evonik Industries) and Toximul (Stepan Company), including Varonic K-210 and Toximul CA 7.5.

According to a preferred embodiment, the ethoxylated amine is selected according to an R group substituent providing suitable solubility to ensure the maintained physical stability of the antimicrobial fatty acid, such as decanoic acid. Although not intended to be limited to a particular theory of the invention, the solubility of the R group of the ethoxylated amine obviates the need for increased ethoxylated amine to antimicrobial agent ratio beyond approximately 3.5:1 to about 5.5:1.

In an embodiment, the ethoxylated cocoamine provides physical stability to a concentrate or use antimicrobial composition, while retaining the solubility and clarity of the concentrate or use solution, and/or without inhibiting action of the fatty acid antimicrobial agent. According to an embodiment of the invention, the composition includes an ethoxylated cocoamine as the primary solubilizing (coupling) or emulsifying agent.

The compositions of the invention contain sufficient ethoxylated amine surfactant to achieve the desired solubility of the use solution without interfering with the efficacy of microbial reduction. The ethoxylated amine can be present in a solid concentrate composition at about 0.2 to about 95 wt-%, about 0.3 to about 95 wt-%, about 0.4 to about 95 wt-%, about 0.2 to about 90 wt-%, about 0.2 to about 60 wt-%, about 1 to about 60 wt-%, about 1 to about 50 wt-%, about 1 to about 30 wt-%, or about 1 to about 20 wt-%. The antimicrobial agent can be present at any of these amounts not as part of a range and/or at any of these amounts not modified by about.

The compositions of the invention contain sufficient ethoxylated amine surfactant to achieve the desired solubility of the use solution without interfering with the efficacy of microbial reduction. The ethoxylated amine can be present in a use composition, such as a use solution at about 0.005 to about 25 wt-%, about 0.01 to about 20 wt-%, about 0.01 to about 5 wt-%, about 0.015 to about 3 wt-%, about 0.03 to about 3 wt-%, about 0.05 to about 15 wt-%, about 0.1 to about 25 wt-%, about 0.1 to about 20 wt-%, about 0.1 to about 10 wt-%, about 0.2 to about 10 wt-%, about 0.4 to about 10 wt-%, about 0.4 to about 5 wt-%, about 0.4 to about 20 wt-%, about 0.4 to about 5 wt-%, about 0.4 to about 4 wt-%, about 0.4 to about 2 wt-%, or about 0.4 to about 1 wt-%. The antimicrobial agent can be present at any of these amounts not as part of a range and/or at any of these amounts not modified by about.

According to an embodiment of the invention the antimicrobial composition comprises, consists of or consists essentially of a nonionic surfactant and a carboxylic acid antimicrobial agent, wherein the nonionic surfactant has a narrow range of HLB values, sufficiently soluble R group, and a surfactant to antimicrobial agent ratio that retains full antimicrobial efficacy of the carboxylic acid antimicrobial agent, such as decanoic acid.

According to a particular embodiment of the invention, the composition comprises about 0.05 wt-% to about 20 wt-% carboxylic acid antimicrobial agent, and about 0.1 wt-% to about 30 wt-% nonionic surfactant, wherein the nonionic surfactant and carboxylic acid antimicrobial agent have a weight ratio of about 5.5:1 to about 3:1 and the composition is clear and has effective antimicrobial activity. According to such an embodiment the carboxylic acid antimicrobial agent is a $C_6$-$C_{16}$ alkyl carboxylic acid, salt or ester thereof, including for example wherein the $C_6$-$C_{12}$ alkyl carboxylic acid comprises octanoic acid, heptanoic acid, nonanoic acid, decanoic acid, dodecanoic acid, myristic acid, isomers thereof, or mixtures thereof. Preferably the nonionic surfactant is an ethoxylated amine and the antimicrobial agent is decanoic acid and the ratio of ethoxylated amine to decanoic acid is about 4.5:1.

According to a further embodiment of the invention, the composition comprises about 0.05 wt-% to about 10 wt-% fatty acid antimicrobial agent, about 0.15 wt-% to about 55 wt-% ethoxylated amine of one of the following formulas:

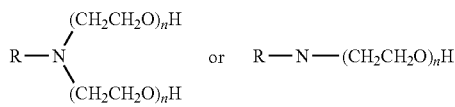

wherein the ethoxylated amine and fatty acid antimicrobial agent have a weight ratio of about 5.5:1 to about 3:1, and wherein the composition is clear and has effective antimicrobial activity. Preferably the fatty acid antimicrobial agent comprises octanoic acid, heptanoic acid, nonanoic acid, decanoic acid, dodecanoic acid, myristic acid, isomers thereof, or mixtures thereof and the ethoxylated amine has a hydrophile-lipohile balance (HLB) from about 7.5 to about 14. More preferably, the HLB of the ethoxylated amine is from about 10 to about 14 and the R group of the ethoxylated amine is a substituent comprising a mixture of saturated and unsaturated fatty acids with 6-18 carbons. More preferably the R group is a substituent derived from coconut oil. Still further, according to an embodiment the ration of ethoxylated amine and fatty acid antimicrobial agent is about 5.5:1 to about 3:1.

Acids or Acidulants

The present compositions can include one or more ingredient to decrease the pH, e.g. one or more acids or acidulants. Suitable acids include organic and inorganic acids. For example, suitable inorganic acids include phosphoric acid, hydrochloric acid, nitric acid, sulfuric acid, sulfamic acid, mixtures thereof, or the like. For example, suitable organic acids include lactic acid, citric acid, propionic acid, acetic acid, hydroxyacetic acid, formic acid, glutaric acid, malic acid, hydroxy propionic acid, succinic acid, glutaric acid, adipic acid, fumaric acid, mixtures thereof, or the like. In an embodiment, the acid includes phosphoric acid, lactic acid, or a mixture thereof. In an embodiment, the acid includes phosphoric acid, lactic acid, hydroxyacetic acid, or a mixture thereof. In an embodiment, the acid includes citric acid, lactic acid, urea hydrochloride, or a mixture thereof.

Solvent

A variety of fluids can be used as the diluting solvent, including water in its liquid form. The compositions of the invention can be formulated to include the diluting solvent (e.g., water) as sold, or the diluting solvent can be added at any time up to the time of use. Preferably, the concentrates of the invention contain little or no diluting solvent as sold. A variety of dilution ratios can be employed, so long as the diluted composition exhibits the desired antimicrobial behavior when applied to the target microbes. The ingredients in the concentrate can represent about 1 to about 99 wt-% of the diluted mixture. As a further guide, the diluted composition preferably contains antimicrobially-active solvent in an amount near the solubility limit of the antimicrobially-active solvent in the diluting solvent. In addition, the diluted antimicrobial compositions preferably are aqueous, contain additional antimicrobial agent, and are clear or quasi-stable. For example, water can be used to dilute an antimicrobial composition to a preferred use concentration of approximately 3%.

According to additional embodiments, the present compositions can include one or more solvents including organic and aqueous solvents. For example, suitable organic solvents include isopropanol, other lower alcohols, glycol ethers, mixtures thereof, or the like. For example, suitable aqueous solvents include water, mixtures of water with the organic solvent, mixtures thereof, or the like. In an embodiment, the solvent includes isopropanol, water, or a mixture thereof.

Surfactant

The present compositions can include one or more surfactants. The surfactant or surfactant admixture can include nonionic, semi-polar nonionic, or anionic surface-active agents; or any combination thereof. Generally, the concentration of surfactant or surfactant mixture useful in use solution compositions fall in the range of from about 0.01 to about 30 wt-%, about 1 to about 30 wt-%, about 2 to about 20 wt-%, or about 5 to about 15 wt-%. These percentages can refer to percentages of the commercially available surfactant composition, which can contain solvents, dyes, odorants, and the like in addition to the actual surfactant. In this case, the percentage of the actual surfactant chemical can be less than the percentages listed. These percentages can refer to the percentage of the actual surfactant chemical.

Surfactant can be present at any of these amounts not as part of a range and/or at any of these amounts not modified by about.

In an embodiment, the surfactant includes anionic surfactant, amphoteric surfactant, nonionic surfactant, or mixture thereof. In a preferred embodiment, the surfactant includes a nonionic surfactant. Nonionic surfactants useful in the invention are generally characterized by the presence of an organic hydrophobic group and an organic hydrophilic group and are typically produced by the condensation of an organic aliphatic, alkyl aromatic, fatty alcohol, or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Further description of suitable nonionic, semi-polar nonionic, or anionic surface-active agents for use according to the compositions of the invention are more fully disclosed in U.S. Pat. No. 7,341,983.

Sequestrant

The present compositions can include one or more sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids, hydroxycarboxylic acids, or aminocarboxylic acids. Chelating agents or sequestrants generally useful in the present compositions include salts or acids of (expressed in acid form) alkyl diamine polyacetic acid-type chelating agents such as ethylenediamine tetraacetic acid (EDTA), hydroxyethylethylethylene diamine triacetic acid (HEDTA), and ethylene triaminepentaacetic acid, phosphonic acid, and phosphonate-type chelating agents among others. Suitable phosphonic acids and phosphonate salts include 1-hydroxy ethylidene-1,1-diphosphonic acid (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; as well as the alkyl metal salts, ammonium salts, or alkyloyl amine salts, such as mono, di, or tetraethanolamine salts.

Adjuvants

The present composition can also include any number of adjuvants, including for example, stabilizing agent, wetting agent, thickener, foaming agent, pigment or dye among any number of constituents which can be added to the composition. Such adjuvants can be preformulated with the present composition or added to the system simultaneously, or even after, the addition of the present composition. The composition can also contain any number of other constituents as necessitated by the application, which are known and which can facilitate the activity of the present compositions. The types and amounts of such adjuvants and/or constituents will be apparent to those skilled in the art.

Solubility of Antimicrobial Agent

Preferred compositions and methods of the invention provide stable antimicrobial compositions that do not experience phase-separation or phase-splitting following application of the composition to a surface. The term "phase" refers to a homogeneous fluid portion that is present in or that can form in a fluid system. The term "phases" refers to the presence of more than one phase in a heterogeneous fluid system. In some embodiments of the invention, the compositions (and in some methods of the invention employing such compositions), specifically the amount of antimicrobially-active solvent and a particular cosolvent or surfactant are combined in a ratio sufficient to form a stable, solution of the antimicrobial composition. Such compositions have a clear appearance, do not experience phase-separation, and do not undergo phase-splitting.

For simplicity, the remainder of this specification discusses compositions according to the invention that retain a clear one-phase mixtures. However, one skilled in the art will appreciate that embodiments of the invention may include a slightly cloudy phase dispersion where the solubility limits of the antimicrobial agents are approached. It is to be understood that compositions having saturated antimicrobial agent solubility could be employed if desired. However, preferred embodiments of the invention achieve antimicrobial agent solubility without having to increase the ratio of surfactant to antimicrobial agent.

Concentrates and Use Solution Compositions

The compositions of the present invention can be formulated by combining the antimicrobially-active agents, the ethoxylated amine, and any other ingredients, which may be combined to form a concentrate or superconcentrate composition, or which can be diluted at the site of use to form a use solution composition.

According to the invention, superconcentrates do not include water as an purposefully added raw material (though water can be present in some of the ingredients). Superconcentrates can be formulated which are both flowable and stable and can be useful to provide small dispensed volumes or individual dosage packs. According to the invention, a solid concentrate composition may be diluted to a use solution prior to application to an object. Primarily for reasons of economics, the concentrate would normally be marketed and an end user would preferably dilute the concentrate with water or an aqueous diluent to a use solution.

The level of active components in the concentrate composition is dependent on the intended dilution factor and the desired activity of the fatty acid antimicrobial. Generally, a dilution of about 0.1 to about 25 ounces of concentrate composition per gallon of diluent (e.g., water) provides a suitable use composition. Higher use dilutions can be employed if elevated use temperature (greater than 25° C.) or extended exposure time (greater than 30 seconds) can be employed. In the typical use locus, the concentrate is diluted with a major proportion of water using commonly available tap or service water.

The compositions of the invention can therefore be formulated and sold for use as is, or as solvent concentrates. If desired, such concentrates can be used full-strength as antimicrobial agents. However, the concentrates typically will be diluted with a fluid (e.g., water) that subsequently forms the aqueous use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

A variety of fluids can be used as the diluting solvent, including water in its liquid form; steam; condensed gases and other supercritical fluids (e.g., CO2). Mixtures of diluting solvents can be used if desired. Preferably, the diluting solvent consists essentially of or consists of water in its liquid form. The remainder of this specification will primarily discuss the use of water in its liquid form as the diluting solvent, it being understood that other suitable fluids could be added to or substituted for water in its liquid form if desired.

Kits

The antimicrobial compositions of the invention can be sold in the form of a kit containing the composition together with suitable directions for carrying out the method of the invention. Such directions typically will include recommended dilution ratios, applications, application techniques and safety warnings.

Methods of Use

The methods of cleaning according to the invention comprise, consist of and/or consist essentially of contacting a surface with the antimicrobial composition of the invention. The antimicrobial compositions can be applied to microbes or to soiled or cleaned surfaces using a variety of methods. For example, the antimicrobial composition can be sprayed or wiped onto a surface; the composition can be caused to flow over the surface, or the surface can be dipped into the composition. The compositions can be formulated as liquids, gels, aerosols, waxes, solids, or powders. If steam or another gaseous diluting solvent is employed, then the compositions can be formulated to be applied in a gaseous state.

The antimicrobial compositions according to the invention can be used for a variety of domestic or industrial applications, e.g., to reduce microbial populations on a surface or object. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials comprising, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials comprising, for example, paper, fiber, woven or nonwoven fabric, soft plastics and elastomers. The compositions of the invention can also be applied to soft surfaces such as food and skin. The compositions are also suitable for application to growing or harvested plant material including leaves, stems, tubers, roots, seeds, and the like.

The antimicrobial compositions according to the invention can be included in products such as sterilants, sanitizers, disinfectants, soap scum remover, lime remover, delimer, hand wash and sanitizer and other cleaners. The compositions have particular utility as a shower cleaner, disinfectant and sanitizer. The antimicrobial compositions can also be used in a variety of healthcare and food service applications.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Several composition formulations were evaluated for disinfecting efficacy according to the invention. The compositions and controls were evaluated for antimicrobial activity against *Staphylococcus aureus* using the procedure set out in the Germicidal Spray Test (GST) method based on AOAC Official Method 961.02 and applicable sections (Germicidal Spray Products as Disinfectants). The revised method is available in: Official Methods of Analysis (2009) 18$^{th}$ Edition, Association of Official Analytical Chemists (AOAC) International, Methods 961.02, Gaithersburg, Md., Chapter 6. The methods used a 5 minute contact time against the *Staphylococcus aureus* at ambient temperature, which according to standard laboratory operating procedure is between 15-30° C.

Materials: The following materials were utilized according to the test methods of the invention.

*Staphylococcus aureus* (ATCC No. 6538).

Varonic K-210, ethoxylated cocoamine 10EO

Decanoic acid (capric acid)

Citric acid, 2-hydroxypropane-1,2,3-tricarboxylic acid, 3-hydroxypentanedioic acid-3 carboxylic acid Colatrope, Isononanoic Acid Tomadol 1-9, alcohol ethoxylate Varonic K-205, ethoxylated cocoamine 5EO Linear alkyl benzene sulfonated (LAS)

Malic acid, hydroxybutanedioic acid

Example 2

Initial formulation testing achieved good cleaning and disinfection properties but poor temperature stability, resulting in the need to identify alternative surfactants for substitution into the formula in order to improve temperature stability. In exploring these alternative surfactants, it was found that the efficacy was greatly affected by changing the hydrophilic-lipophilic balance (HLB) of the surfactant, the R— group of the surfactant, and the ratio of the surfactant to fatty acid, leading to the discovery of a narrow range of HLB values, R groups, and surfactant ratios within the bounds of which the decanoic acid remained efficacious.

Testing Surfactant to Fatty Acid Ratio. Two disinfecting composition formulas were made with varying surfactant to acid ratios as shown in Table 1.

TABLE 1

| Material | Formula 1 | Formula 2 |
| --- | --- | --- |
| Citric Acid | 83.5 | 80.5 |
| Varonic K-210 | 13.5 | 16.5 |
| Decanoic Acid | 3.0 | 3.0 |

The disinfecting composition formulas were run using the Germicidal Spray Test (GST) method against *Staphylococcus aureus* bacteria in 400 ppm hardness water with soap scum soil and fetal bovine serum. The results are shown in Table 2, where a test is passed with greater than 58 negative carriers out of 60.

TABLE 2

| # Negative Carriers/Total Carriers Tested | Replicate 1 | Replicate 2 |
| --- | --- | --- |
| Formula 1 | 60/60 | 60/60 |
| Formula 2 | 56/60 | 53/60 |

The disinfecting composition formula having a surfactant to fatty acid ratio of 4.5 yielded passing results on the GST test. The disinfecting composition formula having an increased surfactant to fatty acid ratio of 5.5 did not pass the GST as a result of failing to successfully kill all of the bacteria.

Example 3

Testing Surfactant HLB Range. Two disinfecting composition formulas were made with surfactants of varying HLB as shown in Table 3. The Formula 1 from Example 2, having an HLB of 13.8 was compared to a surfactant with an HLB of 1.0 using the GST methods. Results are shown in Table 4.

TABLE 3

| Material | Formula 1 | Formula 3 |
| --- | --- | --- |
| Citric Acid | 83.5 | 83.5 |
| Decanoic Acid | 3.0 | 3.0 |
| Varonic K-210 HLB = 13.8 | 13.5 | 0.0 |
| Varonic K-205 HLB = 1.0 | 0.0 | 13.5 |

TABLE 4

| | # Negative Carriers/ Total Carriers Tested |
| --- | --- |
| Formula 1 | 60/60 |
| Formula 3 | 43/60 |

This results demonstrate the use of surfactants in the same ratio to the fatty acid of the disinfecting composition yield, having different HLB, generated significantly different disinfectant efficacy. The use of Formula 3 having a decreased HLB did not successfully kill all of the bacteria.

Example 4

Testing R-Groups of the Surfactant. Three disinfecting composition formulas were made with surfactants with varying R— groups and equal HLBs as shown in Table 5.

TABLE 5

| Material | Formula 1 | Formula 4 | Formula 5 |
| --- | --- | --- | --- |
| Citric Acid | 83.5 | 83.5 | 79.0 |
| Varonic K-210 | 13.5 | 0.0 | 0.0 |
| Tomadol 1-9 | 0.0 | 13.5 | 18.0 |
| Decanoic Acid | 3.0 | 3.0 | 3.0 |

Each formula was diluted into DI water at a concentration of 3% by weight. Observations included the dilution of Formula 1 yielded a clear solution without flakes or cloudiness, whereas the dilution of Formula 4, of the same ratio of surfactant to fatty acid as Formula 1 yielded a cloudy solution. The failure of the decanoic acid to dissolve in the aqueous solution of Formula 4 necessitated the generation of Formula 5, with a higher surfactant to fatty acid ratio in order to dissolve the decanoic acid into solution. Formula 5 yielded a clear solution. The results of the GST are shown in Table 6.

TABLE 6

| | # Negative Carriers/Total Carriers Tested |
| --- | --- |
| Formula 1 | 60/60 |
| Formula 5 | 36/60 |

Table 6 demonstrates that the R group on the surfactant plays a large role in the solubilization action of the fatty acid in an aqueous solution, and some R groups more readily solubilize fatty acids than other R groups. Additionally, solubilization of the fatty acid may significantly increase the ratio of surfactant to fatty acid which can negatively affect the activity of the fatty acid.

This phenomena is most likely due to the miscelles fully absorbing the fatty acid where it is likely to stay, in lieu of going to the surface of the bacteria and thus killing it. The fatty acid will only remain active if solubilized in solution, but still available enough to go after bacteria.

Example 5

Testing Cleaning Power of the Formula. This formula was tested for its cleaning ability against soap scum soil and compared to a disinfecting cleanser Formula 6, shown below.

| Material | Formula 1 | Formula 6 |
| --- | --- | --- |
| Citric Acid | 83.5 | 60.0 |
| Varonic K-210 | 13.5 | |
| Decanoic Acid | 3.0 | |

-continued

| Material | Formula 1 | Formula 6 |
| --- | --- | --- |
| Malic Acid | 0.0 | 30.0 |
| Linear Alkyl Benzene Sulfonate (LAS) | | 10.0 |

Black gloss ceramic tiles were sprayed with a hot mixture of synthetic hard water, casein, sodium tallowate, sodium cocoate, vegetable shortening and clay and then baked for 30 minutes at 200° C. The tiles were then cooled and the reflectance of the resulting soiled surface was measured with a Gardner Micro-Tri-Gloss reflectance meter. The tiles were then sprayed with the product and scrubbed in an apparatus that provided constant normal force onto each tile using a sponge saturated with the product. Each tile was passed a finite number of times with the sponge, rinsed, and reflectance read using the reflectance meter. The before and after reflectance measurements were used along with the measurement taken from an unused tile were compared and the percent change in reflectance was calculated. These percent changes were averaged and compared.

| Detergent | Dilution | Percent Change in Reflectance (average of 4 tiles) | Standard Deviation |
| --- | --- | --- | --- |
| Formula 1 | 3.0% | 85.4 | 17.8 |
| Formula 6 | 3.0% | 13.7 | 3.6 |
| Water | N/A | 7.1 | 2.2 |

The results show that using a different active, such as LAS, in the formula can negatively impact cleaning performance. Formula 1 is considered to be an acceptable cleanser for shower soils.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A solid concentrate antimicrobial composition for cleaning comprising:
    about 0.05 wt-% to about 20 wt-% of at least one carboxylic acid antimicrobial agent, wherein the at least one carboxylic acid antimicrobial agent is decanoic acid; and
    about 0.1 wt-% to about 30 wt-% nonionic surfactant, wherein said nonionic surfactant is an ethoxylated amine;
    wherein the nonionic surfactant and carboxylic acid antimicrobial agent have a weight ratio of about 5.5:1 to about 3:1;
    wherein said ethoxylated amine has a hydrophile-lipophile balance (HLB) from about 7.5 to about 14; and
    wherein upon dilution, the composition produces a clear solution and has effective antimicrobial activity.

2. The composition of claim 1 further comprising a C6-Ci6 alkyl carboxylic acid, salt or ester thereof.

3. The composition of claim 2 wherein said C6-C12 alkyl carboxylic acid comprises octanoic acid, heptanoic acid, nonanoic acid, dodecanoic acid, myristic acid, isomers thereof, or mixtures thereof.

4. The composition of claim 1 further comprising a sequestrant, acidulant, stabilizing agent, wetting agent, thickener, foaming agent, pigment dye or mixtures thereof.

5. The composition of claim 1, wherein said ratio of ethoxylated amine to decanoic acid is about 4.5:1.

6. A solid shower cleaning composition comprising:
    about 0.05 wt-% to about 10 wt-% of at least one fatty acid antimicrobial agent, wherein the at least one fatty acid antimicrobial agent is decanoic acid;
    about 0.15 wt-% to about 55 wt-% ethoxylated amine of one of the following formulas:

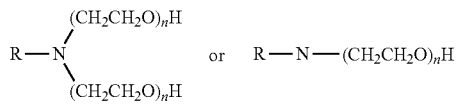

wherein R is selected from the group consisting of a straight alkyl, branched alkyl, or alkylaryl substituent, having from 1 to 24 carbon atoms, and wherein n is from 1 to 20;
    wherein the ethoxylated amine and fatty acid antimicrobial agents being at a weight ratio of about 5.5:1 to about 3:1;
    wherein said ethoxylated amine has a hydrophile-lipophile balance (HLB) from about 7.5 to about 14; and
    wherein the composition produces a clear use solution upon dilution with a solvent and has effective antimicrobial activity.

7. The composition of claim 6 further comprising octanoic acid, heptanoic acid, nonanoic acid, dodecanoic acid, myristic acid, isomers thereof, or mixtures thereof.

8. The composition of claim 6 wherein said HLB is from about 10 to about 14.

9. The composition of claim 6 wherein R is a substituent comprising a mixture of saturated and unsaturated fatty acids with 6-18 carbons.

10. The composition of claim 6 wherein R is substituent derived from coconut oil.

11. The composition of claim 6 wherein said ratio of ethoxylated amine and decanoic acid is about 5.5:1 to about 4:1.

12. The composition of claim 1, wherein the ethoxylated amine is ethoxylated cocoamine 10E0.

13. The composition of claim 6, wherein the composition is highly bio-based, non-irritating, and non-corrosive.

* * * * *

UNITED STATES PATENT AND TRADEMARK OFFICE
CERTIFICATE OF CORRECTION

PATENT NO. : 9,686,981 B2  
APPLICATION NO. : 14/641914  
DATED : June 27, 2017  
INVENTOR(S) : Elizabeth Kiesel et al.

It is certified that error appears in the above-identified patent and that said Letters Patent is hereby corrected as shown below:

In the Claims

In Column 17, Claim 1, Line 52:
DELETE "agent" after the word antimicrobial
INSERT --agents-- after the word antimicrobial In Column 18, Claim 2, Line 4:
DELETE "C6-Ci6" before the word alkyl
INSERT --C6-C16-- before the word alkyl Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*